US007226470B2

(12) United States Patent
Kemény et al.

(10) Patent No.: US 7,226,470 B2
(45) Date of Patent: Jun. 5, 2007

(54) PHOTOTHERAPEUTICAL APPARATUS AND METHOD FOR THE TREATMENT AND PREVENTION OF DISEASES OF BODY CAVITIES

(75) Inventors: Lajos Kemény, Szeged (HU); Zsolt Bor, Szeged (HU); Gábor Szabó, Szeged (HU); Ferenc Ignácz, Melykut (HU); Béla Rácz, Szeged (HU); Attila Dobozy, Szeged (HU)

(73) Assignee: Rhinolight Corporation, Irvine, CA (US)

( * ) Notice: Subject to any disclaimer, the term of this patent is extended or adjusted under 35 U.S.C. 154(b) by 108 days.

(21) Appl. No.: 10/410,690

(22) Filed: Apr. 9, 2003

(65) Prior Publication Data
US 2004/0204747 A1    Oct. 14, 2004

Related U.S. Application Data

(63) Continuation of application No. PCT/HU01/00102, filed on Oct. 24, 2001.

(30) Foreign Application Priority Data
Aug. 10, 2001    (HU)    .................................. P0103279

(51) Int. Cl.
*A61N 5/06*    (2006.01)
(52) U.S. Cl. .......................... 607/94; 128/898; 607/88; 607/92
(58) Field of Classification Search .................. 606/2, 606/6, 9, 10, 13; 607/88–94; 128/898; 605/6

See application file for complete search history.

(56) References Cited

U.S. PATENT DOCUMENTS
1,616,722  A    2/1927    Vernon
(Continued)

FOREIGN PATENT DOCUMENTS
EP    0 435 506 A2    12/1990
(Continued)

OTHER PUBLICATIONS
Specification Sheet, Hilltech from Aug. 8, 2001 web page on quartz, short arc lamps.*
(Continued)

*Primary Examiner*—Henry M Johnson, III
(74) *Attorney, Agent, or Firm*—Jonathan W. Hallman; MacPherson Kwok Chen & Heid LLP

(57) ABSTRACT

A phototherapeutical apparatus and method are described. The apparatus includes an ultraviolet light source, an optical guidance system, and a patient interface. The patient interface is insertable at least partially into a body cavity and is operable to apply the guided ultraviolet light to a tissue surface of a body cavity. The method includes providing the phototherapeutical apparatus, preparing for the application of the phototherapeutical apparatus, inserting the patient interface at least partially into a body cavity, and applying the ultraviolet light by the patient interface to a tissue surface of a body cavity, wherein the tissue of the body cavity has an inflammatory or a hyperproliferative disease. The inflammatory diseases include rhinitis, sinusitis and rhinosinusitis. A photochemotherapeutical method is also described, using photosensitizing substances, such as psoralen before treatment with ultraviolet light. The phototherapeutical method is also effective for the prevention of inflammatory or hyperproliferative diseases.

28 Claims, 12 Drawing Sheets

U.S. PATENT DOCUMENTS

| | | | |
|---|---|---|---|
| 1,677,016 A | | 7/1928 | Berry |
| 1,782,906 A | | 11/1930 | Newman |
| 1,800,277 A | | 4/1931 | Boerstler |
| 2,227,422 A | | 1/1941 | Boerstler |
| 4,762,120 A | * | 8/1988 | Hussein ..................... 600/136 |
| 4,765,322 A | | 8/1988 | Charmillot et al. |
| 4,782,819 A | | 11/1988 | Adair |
| 4,842,356 A | | 6/1989 | Mori |
| 4,862,886 A | | 9/1989 | Clarke et al. |
| 4,899,732 A | * | 2/1990 | Cohen ......................... 600/146 |
| 4,930,504 A | * | 6/1990 | Diamantopoulos et al. ... 607/88 |
| 5,113,119 A | * | 5/1992 | Niemann et al. ........... 313/638 |
| 5,119,461 A | | 6/1992 | Beyer et al. |
| 5,292,346 A | | 3/1994 | Ceravolo |
| 5,344,433 A | | 9/1994 | Talmore |
| 5,405,368 A | | 4/1995 | Eckhouse |
| 5,439,462 A | | 8/1995 | Bille et al. |
| 5,445,608 A | | 8/1995 | Chen et al. |
| 5,620,478 A | | 4/1997 | Eckhouse |
| 5,626,631 A | | 5/1997 | Eckhouse |
| 5,683,436 A | * | 11/1997 | Mendes et al. ............... 607/88 |
| 5,720,772 A | | 2/1998 | Eckhouse |
| 5,755,751 A | | 5/1998 | Eckhouse |
| 5,843,143 A | | 12/1998 | Whitehurst |
| 5,854,535 A | * | 12/1998 | Hohlfeld et al. ........... 313/636 |
| 5,855,595 A | | 1/1999 | Fujishima et al. |
| 5,865,829 A | * | 2/1999 | Kitajima ..................... 607/88 |
| 5,919,217 A | | 7/1999 | Hughes |
| 5,925,034 A | | 7/1999 | Buckley et al. |
| 5,989,283 A | | 11/1999 | Wilkens |
| 6,174,325 B1 | | 1/2001 | Eckhouse |
| 6,290,713 B1 | | 9/2001 | Russell |
| 6,376,988 B1 | * | 4/2002 | Mukai et al. ............... 313/641 |
| 6,413,268 B1 | * | 7/2002 | Hartman ...................... 607/94 |
| 6,436,127 B1 | | 8/2002 | Anderson et al. |
| 6,447,537 B1 | | 9/2002 | Hartman |
| 6,482,201 B1 | * | 11/2002 | Olsen et al. .................. 606/41 |
| 6,530,919 B1 | | 3/2003 | Chodorow et al. |
| 6,641,578 B2 | * | 11/2003 | Mukai ............................ 606/9 |
| 6,692,486 B2 | * | 2/2004 | Jaafar et al. .................... 606/7 |
| 2002/0161418 A1 | | 10/2002 | Wilkens et al. |

FOREIGN PATENT DOCUMENTS

| | | |
|---|---|---|
| EP | 0 435 506 A3 | 12/1990 |
| RU | 2045971 C1 | 10/1995 |
| RU | 2169022 C1 | 6/2001 |
| WO | 98/22184 | 5/1998 |
| WO | 96/36396 | 11/1999 |
| WO | 02/13905 A1 | 2/2002 |

OTHER PUBLICATIONS

P.H. Howarth, M. Salagean, and D. Dokic, "Allergic rhinitis: not purely a histamine-related disease," *Allergy*, 2000, vol. 55, pp. 7-16.

J. Wayne Streilein and Paul R. Bergstresser, "Genetic basis of ultraviolet-B effects on contact hypersensitivity," *Immunogenetics*, 1988, vol. 27, pp. 252-258.

Lajos Kemény, MD, PhD, Béla Bónis, MD, Atilla Dobozy, MD, PhD, Zsolt Bor, PhD, Gábor Szabó, PhD, Ferenc Ignácz, PhD, and Szeged, "308-nm Excimer Laser Therapy for Psoriasis," *Arch. Dermatol.*, vol. 137, 2001, pp. 95-96.

M. Folwaczny, A. Mehl, C. Haffner, and R. Hickel, "Substance removal on teeth with and without calculus using 308 nm XeCl excimer laser radiation," *J. Clin. Periodontol*, 1999, vol. 26, pp. 306-312.

Ittai Neuman, MD and Yehuda Finkelstein, MD, "Narrow-band red light phototherapy in perennial allergic rhinits and nasal polyposis," *Annals of Allergy, Asthma, & Immunology*, 1997, vol. 78, pp. 399-406.

Matthias Folwaczy, Dr. med. dent., Tim Liesenhoff, Dr. med., Norbert Lehn, Prof. Dr. med., and Hans-Henning Horch, Prof. Dr. med., Dr. med. dent., "Bacterial Action of 308 nm Excimer-Laser Radiation: An In Vitro Investigation," *Journal of Endodontics*, 1998, vol. 24 No. 12, pp. 781-785.

M. Csato, Anna Sz, Kenderessy and A. Dobozy, "Enhancement of *Cadida albicans* killing activity of separated human epidermal cells by ultraviolet radiation," *British Journal of Dermatology*, 1987, vol. 116, pp. 469-475.

Béla Bónis, Lajos Kemény, Attila Dobozy, Zsolt Bor, Gábor Szabó, Ferenc Ignácz, "308 nm UVB excimer laser for psoriasis," *The Lancet*, 1997, vol. 350, p. 1552.

Pravit Asawanonda, MD, R. Rox Anderson, MD, Yuchiao Chang, PhD, Charles R. Taylor, MD, "308-nm Excimer Laser for the Treatment of Psoriasis," *Arch. Dermatol.*, vol. 136, 2000, pp. 619-624.

International Programme on Chemical Safety, "Ultraviolet Radiation," 1994, 256 pages.

PCT Search Report PCT/HU01/00102.

Early American Energy Medicine, *Actinotherapy Technique - Part II*, Hanovia, 1933, 79 pages. http://www.meridianinstitute.com/eaem/hanovia /hanpart2.html.

Russian Office Action for Application No. 2004104624/14(005059) filed Oct. 24, 2001.

Abraham R. Hollender, M.D. et al., "The Role of Ultra-Violet Light in the Treatment of Perennial and Seasonal Hay Fever," *The Eye, Ear, Nose and Throat Monthly*, pp. 327-330 (Jul. 1924).

A.R. Hollender & M.H. Cottle, "Further Studies in Hay Fever and Asthma with Special Reference to Quartz Ray Therapy," *The Medical Herald and Physiotherapist*, vol. XLIV, pp. 153-160 (Jul. 1925).

"Physics and Therapeutic Action of Radiant Heat Rays," *The Eye, Ear, Nose and Throat Monthly*, pp. 38-41 (Feb. 1925).

T.H. Plank, "Sinusitis," *The Medical Herald*, pp. 220-221 (circa 1928).

Ruxiong Cai, et al., "Induction of Cytotoxicity by Photoexcited $TIO_2$ Particles," *Cancer Research*, Apr. 15, 1992, vol. 52, pp. 2346-2348.

Pin-Ching Maness, et al., "Bacterial Activity of Photocatalytic $TIO_2$ Reaction: toward an Understanding of Its Killing Mechanism," *Applied and Environmental Microbiology*, Sep. 1999, vol. 65, No. 9, pp. 4094-4098.

file:///C/GFX/rhinoea2/img.7html [Jun. 28, 2004 11:32:37].

\* cited by examiner

PHOTOTHERAPEUTICAL APPARATUS AND METHOD FOR THE TREATMENT AND PREVENTION OF DISEASES OF BODY CAVITIES

CROSS REFERENCE TO RELATED APPLICATIONS

The present application is a continuation of PCT International Application No. PCT/HU01/00102, filed on Oct. 24, 2001, which claims priority from Hungarian Patent Application No. P 0103279, filed Aug. 10, 2001.

BACKGROUND

1. Field of Invention

The present invention relates to the treatment and prevention of inflammatory and hyperproliferative diseases of body cavities, more particularly to the treatment and prevention of diseases of the nasal cavity by phototherapeutical methods.

2. Description of Related Art

The treatment and prevention of inflammatory diseases of the nasal mucous membrane and paranasal sinuses is an unsolved problem. These diseases include allergic rhinitis, commonly referred to as hay fever, vasomotor rhinitis, non-allergic eosinophilic rhinitis, chronic sinusitis, which is the inflammation of the paranasal sinuses, and nasal polyps.

Rhinitis is an inflammatory disorder of the nasal mucous membrane, which is characterized by nasal itch, sneeze, nose running, nasal blockage, and rarely by loss of smelling. The inflammation of the nasal mucous membrane is frequently associated with the inflammation of the paranasal sinuses (rhinosinusitis, chronic sinusitis). As a consequence of the frequent and persistent inflammation of the mucous membrane hyperproliferative lesions, or so-called polyps develop on the mucous membrane.

One characteristic disease is the allergic rhinitis, commonly referred to as hay fever. The allergic rhinitis is the most frequent allergic disease affecting 10–20% of the population. The number of patients with allergic rhinitis, especially in the well developed industrial countries increased very rapidly in the last few years. Because of the high number of patients the direct and indirect costs of this disease are great.

Although hay fever is not a very severe disease, its unpleasant symptoms worsen the quality of life considerably. Hay fever is frequently associated with allergic conjunctivitis and sometimes with general symptoms. The symptoms last only for a few months in some patients (seasonal rhinitis), while in others they last the whole year (perennial rhinitis).

The symptoms of the allergic diseases develop as follows. An allergen enters the body and induces the production of a specific IgE, which binds to specific receptors on the surface of mast cells. After subsequent exposure the allergen crosslinks the IgE receptors, resulting in mediator release from the mast cells. These mediators are responsible for the development of the symptoms in patient.

As a result of this activation histamine and other pre-formed mediators are released from the mast cells. In the mast cells new inflammatory mediators are produced attracting further inflammatory cells into the mucous membrane (Howarth PH, Salagean M, Dokic D: Allergic rhinitis: not purely a histamine-related disease. Allergy 55: 7–16, 2000).

At present there is no known treatment for rhinitis. The increased number of inflammatory cells in the nasal mucous membrane release mediators, which are responsible for the clinical symptoms. Often antihistamines are used locally or systemically for the blocking of the released mediators. Sodium cromoglycate is available for the inhibition of the release of mediators. Finally, corticosteroids are used locally or systemically for the blocking of the synthesis of new mediators. In special cases a desensitizing therapy might be used. The pathogenesis of the development of the clinical symptoms is already well known. However, the presently available drugs often do not eliminate the symptoms. Therefore, every new method for the treatment of this disease has a great medical significance.

A further characteristic disease is vasomotor rhinitis. Vasomotor rhinitis is an inflammatory disorder of the nasal mucous membrane with unknown origin. The clinical symptoms are largely similar to that of allergic rhinitis: permanent nasal blockage, nasal itch, sneeze, nose running, and rarely loss of smelling. Mastocyte-activating mediators cause the symptoms. These are released from the nerve endings of the nasal mucous membrane upon irritation.

A further characteristic disease is the nonallergic eosinophilic rhinitis. This disease is characterized by the high number of eosinophils in the nasal secretions and by the lack of an allergic origin. The disease is frequently associated with the development of nasal polyps, the hyperproliferative condition of the nasal mucous membrane. The clinical symptoms are the same as in allergic rhinitis.

Additional diseases are rhinosinusitis and sinusitis. The inflammation of the paranasal sinuses is frequently associated with the inflammatory condition of the nasal mucous membrane (nasosinusitis). The isolated inflammation of the paranasal sinuses is also a frequent disease (sinusitis). This disease has often an allergic origin, although its exact cause remains unknown. There is no well-tested treatment, thus usually the same therapy is used as for rhinitis.

Ultraviolet light has been used for more than twenty years for the treatment of allergic and auto-immune skin diseases. In various treatments and procedures ultraviolet-B light (280 nm–320 nm) and ultraviolet-A light (320 mn–400 nm) is used typically. The ultraviolet light inhibits the antigen-induced cellular immune response and is able to induce tolerance (Streilein J W, Bergstresser P R: Genetic basis of ultraviolet-B on contact hypersensitivity. Immunogenetics 27: 252–258, 1988).

The ultraviolet light suppresses the immune reaction by inhibiting the antigen presentation and by inducing T-cell apoptosis. Irradiation of the skin with ultraviolet-B light or ultraviolet-A light on an area previously photosensitized by psoralen is known to inhibit the immunological processes in the skin. For the treatment of skin diseases there are a number of phototherapeutical devices available.

These phototherapeutical devices include ultraviolet light sources. These light sources might be classified based on, for example, their operational principle, output energy or power, mode of operation (impulse or continuous), and whether they are emitting monochromatic or multiwavelength light.

In early treatments broad band ultraviolet B (BB-UVB) light sources were used. In recent years more efficient narrow band ultraviolet B (NB-UVB) light sources became popular (Degitz K, Messer G, Plewig G, Röcken M: Schmalspektrum-UVB 311 nm versus Breitspektrum-UVB. Neue Entwicklungen in der Phototherapie. Hautarzt 49: 795–806, 1998).

Our previous investigations of psoriatic patients indicated that the 308 nm xenon chloride excimer laser is more effective for phototherapeutical treatments than the NB-UVB light sources (Bónis B, Kemény L, Dobozy A, Bor Zs, Szabó G, Ignácz F: 308 nm UVB excimer laser for psoriasis. Lancet 35: 1522, 1997; Kemény L, Bónis B, Dobozy A, Bor Z, Szabo G, Ignacz F: 308-nm excimer laser therapy for psoriasis. Arch Dermatol. 137: 95–96, 2001).

Phototherapeutical treatments improved significantly with the appearance of ultraviolet light delivering optical systems. Such an ultraviolet light delivering phototherapeutical system with fiber optic is used in the Saalmann Cup instrument, in which the concentrated ultraviolet light is coupled into a fiber optic cable. Therefore, it is suitable for the treatment of smaller lesions of the skin or mucous membrane (Taube K M, Fiedler H: Hochkonzentrierte UV Bestrahlung kleiner Hautbezirke mit einem neuen Punktstrahler. Grundlagen und klinische Ergebnisse. Deutsche Dermatologe, 10: 1453, 1992).

However, the Saalmann Cup can not be introduced into smaller body cavities because of its large contact area and because of the thickness of the used fiber optic cable. This device can be used in body cavities where the distal end of the fiber optic cable and the area to be treated can be visually controlled, such as the oral cavity. For this reason, this device is unsuitable for the treatment of body areas, which cannot be visually controlled, such as the nasal and paranasal mucous membrane, the gastrointestinal, and the urogenital mucous membrane.

Although ultraviolet light has been used for the treatment of hyperproliferative and inflammatory skin diseases for many years, it has not been used for the treatment of common, immunologically mediated disorders of the nasal mucous membrane. Neuman and Finkelstein used narrowband, low energy, red-light phototherapy for the treatment of the nasal mucous membrane and they found it effective for perennial allergic rhinitis and for nasal polyposis (Neuman I, Finkelstein Y Narrow-band red light phototherapy in perennial allergic rhinitis and nasal polyposis. Ann Allergy Asthma Immunol 78: 399–406, 1997).

There are a number of ultraviolet light delivery systems, which use lasers. For example, the light of the 308 nm xenon chloride excimer laser can be guided by fiber optic cable for the cleaning of root canals by ablation (Folwaczny M, Mehl A, Haffner C, Hickel R: Substance removal on teeth with and without calculus using 308 nm XeCl excimer laser radiation. An in vitro investigation. J. Clin. Periodontol 26: 306–12, 1999). The 308 nm xenon chloride excimer laser is also suitable to treat artherosclerosis by treating the blood vessel walls (U.S. Pat. No. 4,686,979), or to enhance the cardiac oxygenization with transmyocardial laser revascularisation (U.S. Pat. No. 5,976,124), or inhibiting neovascularisation during angioplasty by destroying myocardial cells (U.S. Pat. No. 5,053,033).

These systems share the common feature that the high-energy ultraviolet light at the end of the light delivering system is focused on small areas of only a few hundred microns in diameter. This intense ultraviolet light carries out its effect by breaking some of the chemical bonds. However, the intense ultraviolet light damages the tissues with its ablative effect.

It is also known that larger skin lesions can be treated by using a number of small fiber optic cables (U.S. Pat. No. 6,071,302; WO9607451, Asawanonda P, Anderson R R, Chang Y, Taylor C R: 308-nm excimer laser for the treatment of psoriasis: a dose-response study. Arch Dermatol 136: 619–24, 2000).

Phototherapeutical systems attached to endoscopes are also used for the photodynamic treatment of tumors, such as bladder carcinoma or bronchial cancer. However, in these instruments no ultraviolet light is used, and they have special distal ends for tumor treatment (U.S. Pat. Nos. 4,313,431; 4,612,938; 4,676,231; 4,998,930; 5,146,917).

At present, the phototherapeutical systems delivering ultraviolet light consist of a hand piece specifically shaped to a special problem. As such, they are either unsuitable or inconvenient for the treatment of small body cavities such as the nasal cavity with visual control.

Finally, only the light of small concentrated ultraviolet light sources can be coupled with good efficiency into thin optical fiber cables, which have a diameter of a few tenth of millimeter. Ultraviolet lasers are suitable for this purpose, but they are expensive.

SUMMARY

Briefly and generally, embodiments of a phototherapeutical apparatus are described, the apparatus including: an ultraviolet light source, operable to generate ultraviolet light, an optical guidance system, operable to receive and guide the ultraviolet light of the light source, and a patient interface, operable to receive the guided light from the optical guidance system, wherein the patient interface is insertable at least partially into a body cavity and is operable to apply the guided ultraviolet light to a tissue surface of a body cavity.

Further, embodiments of a method of treating diseases is described. The method includes providing a phototherapeutical apparatus, which contains an ultraviolet light source, an optical guidance system, coupled to the ultraviolet light source, and a patient interface, coupled to the optical guidance system. The method further includes preparing for the application of the phototherapeutical apparatus, inserting at least partially the patient interface into a body cavity, generating ultraviolet light with the ultraviolet light source, coupling the generated ultraviolet light into the patient interface through the optical guidance system, and applying the ultraviolet light by the patient interface to a tissue surface of a body cavity, wherein the tissue of the body cavity has an inflammatory disease or a hyperproliferative disease.

Examples of inflammatory diseases include the inflammatory diseases of the nasal cavity. Research showed that single or repeated irradiation of the nasal mucous membrane and paranasal sinuses with ultraviolet light with different wavelengths (UVB and UVA) inhibit the clinical symptoms of rhinitis, sinusitis and rhinosinusitis and result the regression of nasal polyps.

In some embodiments of the phototherapeutical method photochemotherapeutical methods are included, such as using photosensitizing substances. Psoralen is an example of photosensitizing substances.

The phototherapeutical apparatus is also effective for the prevention of inflammatory diseases or hyperproliferative diseases. In these embodiments of the method ultraviolet phototherapy is applied before the appearance of clinical symptoms of the disease.

BRIEF DESCRIPTION OF DRAWINGS

For a more complete understanding of the present invention and for further features and advantages, reference is now made to the following description taken in conjunction with the accompanying drawings.

DETAILED DESCRIPTION

Embodiments of the present invention and their advantages are best understood by referring to FIGS. 1–12 of the drawings. Like numerals are used for like and corresponding parts of the various drawings.

The Phototherapeutical Apparatus

The phototherapeutical apparatus, according to embodiments of the present invention is suited for the treatment and prevention of common inflammatory diseases of the body. In some applications the phototherapeutical apparatus is used for the treatment and prevention of the diseases of a nasal mucous membrane and paranasal sinuses such as allergic rhinitis (hay fever), vasomotor rhinitis, nonallergic eosinophilic rhinitis, chronic sinusitis (inflammation in the paranasal sinuses), or nasal polyps with ultraviolet light. In other applications the phototherapeutical apparatus is used for the treatment and prevention of the diseases of a mouth cavity, a throat, an esophagus, a stomach, a small intestine, a large intestine, a gastrointestinal tract, a rectum, an ear, a trachea, a urogenital tract, a portio, a uterus, and a conjunctiva.

Figure 1:
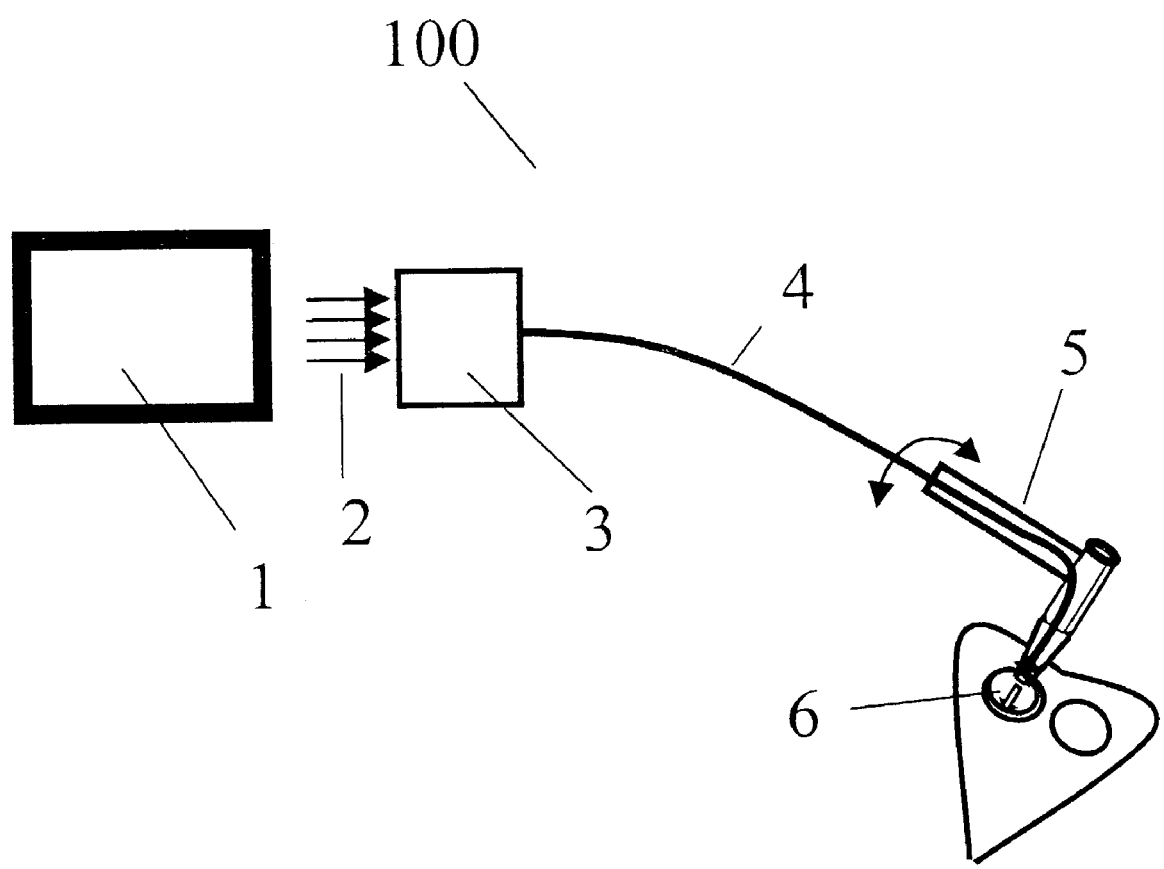
FIG. 1 illustrates an embodiment of the phototherapeutical apparatus according to the invention.

FIG. 1 illustrates a phototerapeutical apparatus 100, according to an embodiment of the invention. Phototerapeutical apparatus 100 includes a ultraviolet light source 1, which generates ultraviolet light beam 2. Ultraviolet light beam 2 enters into an optical coupling unit 3, wherein the ultraviolet light is focused. The focused ultraviolet light is coupled by optical coupling unit 3 into an optical guidance system 4. Optical guidance system 4 guides the ultraviolet light into a patient interface 5. Patient interface 5 is insertable at least partially into a body cavity, where it applies the ultraviolet light to a tissue surface of a body cavity. FIG. 1 illustrates an embodiment, where the body cavity is the nasal cavity and the patient interface is inserted through a nostril 6.

In some embodiments ultraviolet light source 1 generates a continuous ultraviolet light, in others a slowly oscillating ultraviolet light. For example, in some embodiments the frequency of oscillations can be below about 10 Hertz. In various embodiments the continuous ultraviolet light and slowly oscillating ultraviolet light will be jointly referred to as quasi-continuous ultraviolet light.

Ultraviolet light source 1 can be, for example, a monochromatic light source or a multiwavelength light source.

A variety of monochromatic light sources, such as lasers, can be used as ultraviolet light source 1, among others xenon chloride laser, nitrogen laser, frequency multiplied NdYaG laser, any solid state laser, xenon fluoride excimer laser, any type of UV diode lasers or other lasers emitting light in the UV spectrum. Multiwavelength ultraviolet light sources include, for example, discharge lamps, arc lamps filled with xenon, mercury vapour, xenon and mercury vapour, fluorescent lamps, and UV light emitting diodes (UV-LEDs).

The generated ultraviolet light can have a wavelength in the ultraviolet-B (280 nm–320 nm) and ultraviolet-A (320 nm–400 nm) part of the spectrum.

Figure 2:
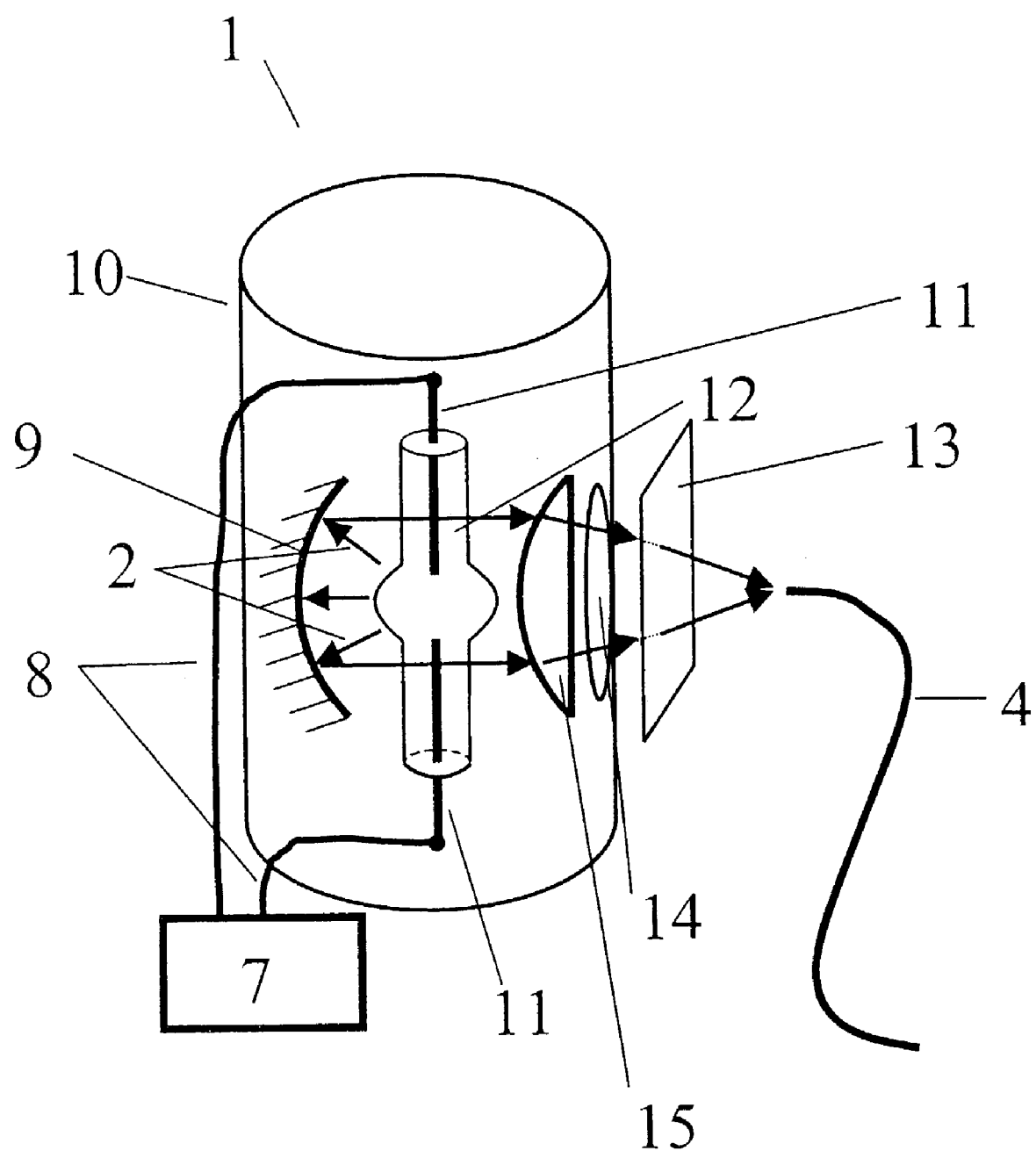
FIG. 2 illustrates an exemplary implementation of the ultraviolet light source according to an embodiment of the invention.

FIG. 2 illustrates a particular ultraviolet light source 1 according to embodiments of the invention. An electric power supply unit 7 is connected to electrodes 11 by wires 8. Electrodes 11 enter the internal space of quartz bulb 12, which is filled with gas. The electric power, provided by electric power supply 7 causes an electric discharge in the gas. During this discharge light is generated. The wavelength of the light depends, among others, on the chemical composition of the gas. With a suitable choice of the chemical composition of the gas the generated light will have a wavenlength in the ultraviolet. In some embodiments the gas or gas mixture in quartz bulb 12 can include xenon, argon, and mercury vapour, and any other gas that emit light at least partially in the ultraviolet spectrum. Part of the ultraviolet light, generated in the internal space, propagates directly towards focusing lens 15. Other portions of the generated ultraviolet light propagate in other directions. Part of these portions are reflected by concave mirror 9 toward focusing lens 15. Focusing lens 15 focuses all incoming ultraviolet lights efficiently into an ultraviolet light beam 2. The focused ultraviolet light beam 2 leaves housing 10 through an output opening 14 and reaches an optical filter 13. In some embodiments optical filter 13 transmits ultraviolet A, or ultraviolet B, or both types of rays. From optical filter 13 the filtered and focused ultraviolet light beam 2 is coupled into an optical guidance system 4.

The volume of the discharge in quartz bulb 12 varies in the range of about 1 $mm^3$ to about tenth of $mm^3$. In some embodiments the discharge volume is positioned approximately in the focus of concave mirror 9, so concave mirror 9 can efficiently focus the emitted ultraviolet light onto focusing lens 15.

Figure 3:
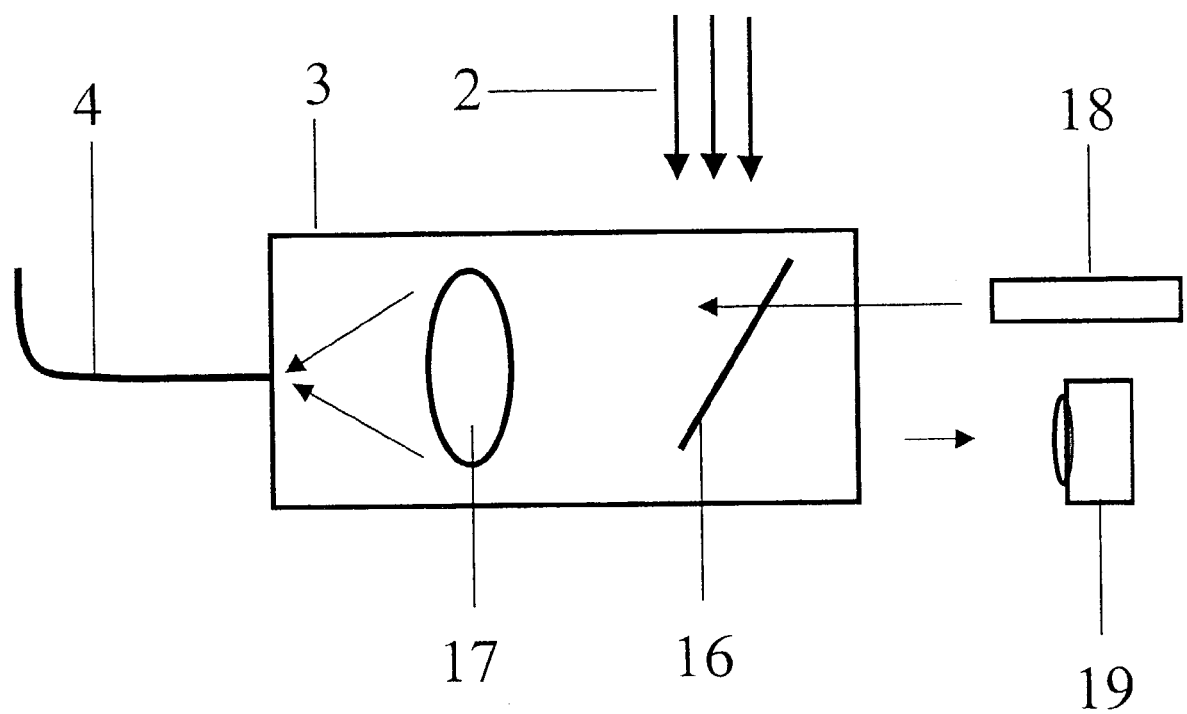
FIG. 3 illustrates an exemplary implementation of the optical coupling unit according to an embodiment of the invention.

FIG. 3 illustrates an embodiment of optical coupling 3. Ultraviolet light beam 2 entering optical coupling unit 3 is directed by a dichroic mirror 16 into optical guidance system 4 through a lens system 17. Dichroic mirror 16 simultaneously performs a spectral filtering of ultraviolet light beam 2.

In some embodiments a targeting light source 18 is employed to guide and assist the application of the ultraviolet light to the intended tissue surface, as in some embodiments the ultraviolet light beam itself may have no component in the visible spectrum. Targeting light source 18 can be, for example, a HeNe laser or a light diode emitting red light or that of any other colour. The light of targeting light source 18 also passes through dichroic mirror 16, so the targeting light also enters optical guidance system 4 through lens system 17. In some embodiments optical guidance system 4 is also applicable to guide back reflected light, reflected from the site of application. The reflected light passes dichroic mirror 16 and can be detected through an observing optical device 19 to assist the application of the phototerapeutical device.

Optical guidance system 4 can be, for example, an optical cable or arm suitable to guide ultraviolet light. The optical cable or arm can be formed of any one of a large number of known suitable materials, among others quartz glass or capillary tubes filled with a liquid capable of guiding ultraviolet light, wherein the internal surface of the capillary tubes are covered with ultraviolet reflecting material. The diameter of the optical cable can be between about 1 micron and about 10 mm. In some embodiments optical guidance system 4 also performs the spectral filtering of ultraviolet light beam 2.

Figure 4:
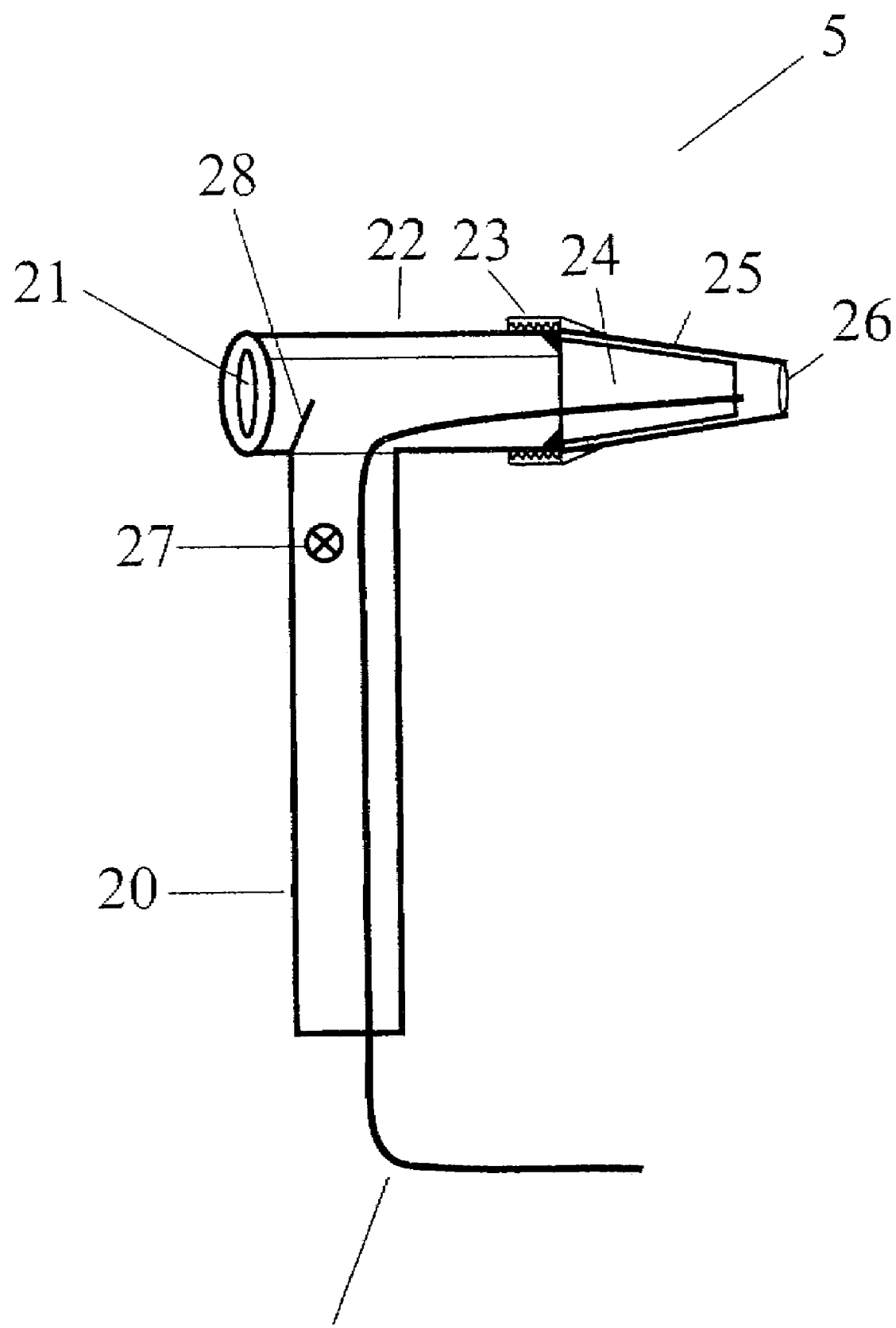
FIG. 4 illustrates an exemplary implementation of the patient interface according to an embodiment of the invention.

FIG. 4 illustrates an embodiment of patient interface 5, suitable for the treatment of the nasal mucous membrane and paranasal sinuses. Patient interface 5 is suited to be positioned at least partially in the nostril and guide the ultraviolet light onto the tissue surface to be treated. Many variations of patient interface 5 can be constructed and are meant to be within the scope of the invention.

In the embodiment of FIG. 4 optical guidance system 4 is attached to handgrip 20. The guided ultraviolet light enters from optical guidance system 4 through handgrip 20 into optical tube 22 and propagates into a tapered end piece 24. A head 25 of patient interface 5 is coupled to optical tube 22 by a fastener 23. An illuminating light source 27 is included to illuminate the area of the tissue surface to be treated. Illuminating light source 27 is built into handgrip 20, and can be powered by either an internal or an external power supply unit. Mirror 28 reflects the illuminating light of illuminating light source 27 onto the tissue surface to be treated. The ultraviolet light, the illuminating light, and, if necessary, the targeting light propagate through output opening 26 onto the tissue surface to be treated. The end of patient interface 5, where the ultraviolet light leaves patient interface 5 is sometimes referred to as the distal end. In the present embodiment the distal end is where output opening 26 is positioned. A magnifying glass 21 mounted onto patient interface 5 provides visual control of the application of the ultraviolet light of phototherapeutical apparatus 100.

Figure 5:
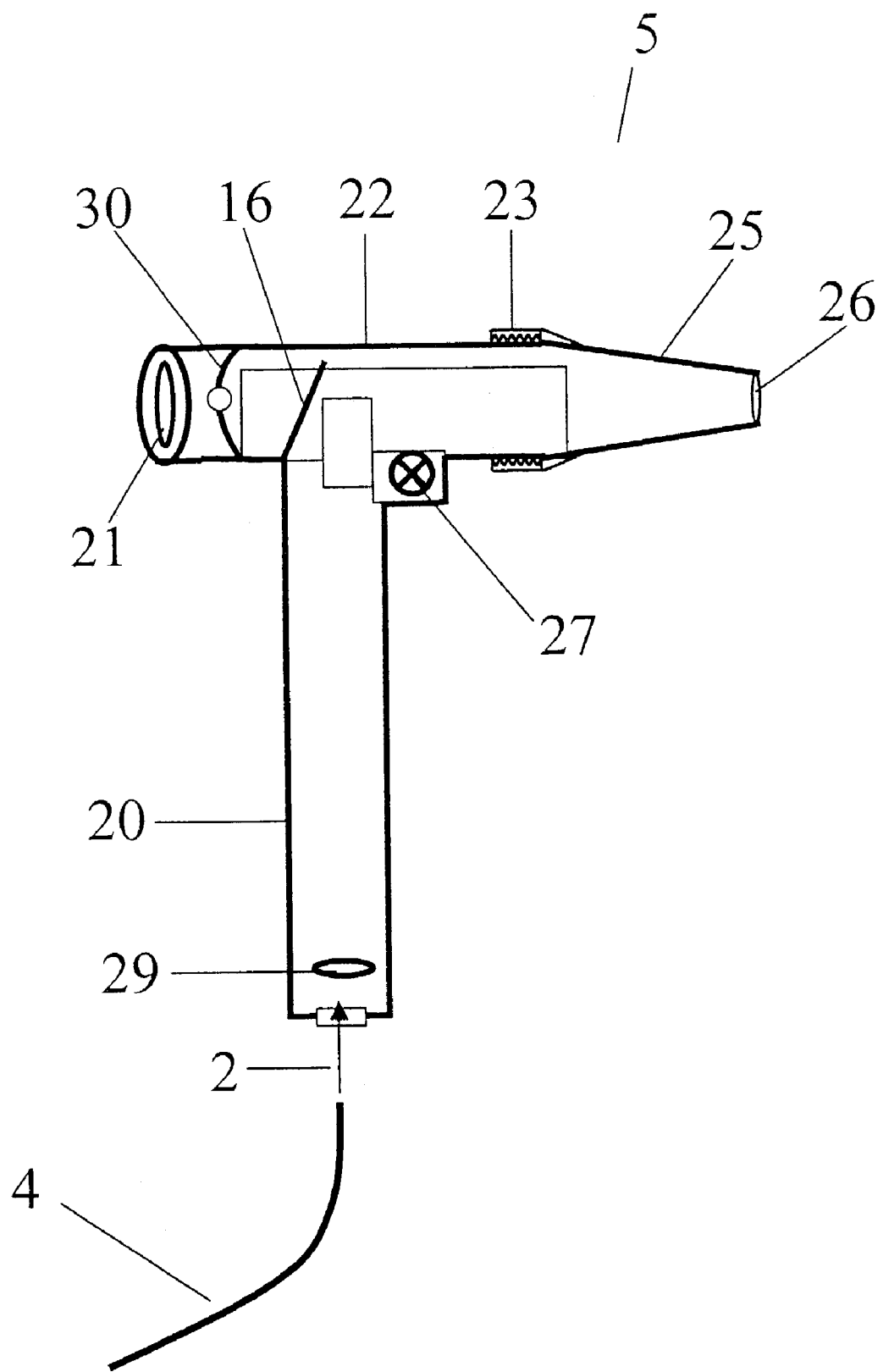
FIG. 5 illustrates an exemplary implementation of the patient interface according to an embodiment of the invention.

FIG. 5 shows another embodiment of patient interface 5, wherein the ultraviolet light beam 2 enters from optical guidance system 4 through a lens 29 of handgrip 20. Ultraviolet light beam 2 is then reflected on dichroic mirror 16, which is mounted inside optical tube 22, and leaves patient interface 5 through output opening 26 of head 25. In this embodiment illuminating light source 27 is mounted inside handgrip 20. The illuminating light passes through dichroic mirror 16 and is reflected by concave holed mirror 30 to illuminate the tissue surface to be treated.

In various embodiments external illuminating light sources are applied to illuminate the tissue area to be treated.

Figure 6:
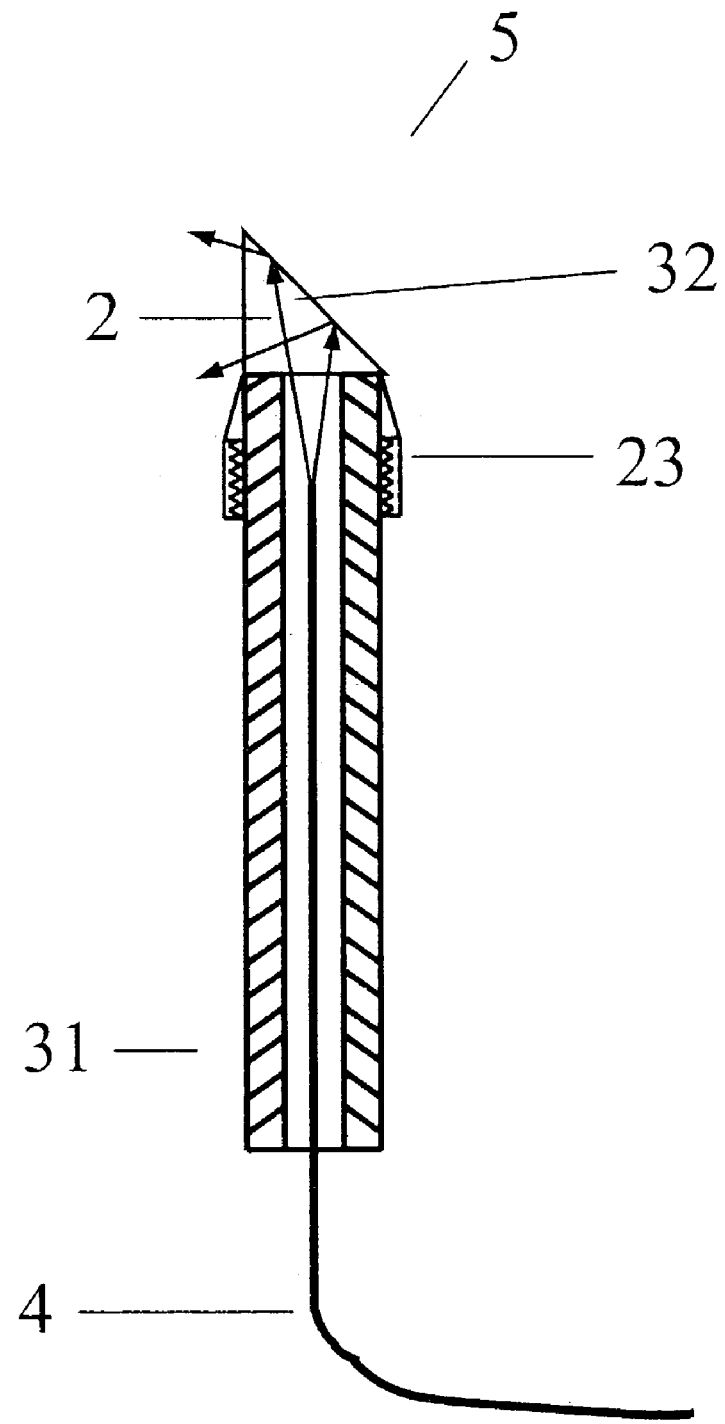
FIG. 6 illustrates an exemplary implementation of the patient interface according to an embodiment of the invention.

FIG. 6 illustrates another embodiment of patient interface 5. In this embodiment optical guidance system 4 is coupled into a pen-shaped handgrip 31. Ultraviolet light beam 2 enters pen-shaped hand grip 31 and is reflected by flat surface treating head 32. Flat surface treating head can include, among others, a quartz prism or a flat mirror. Flat surface treating head 32 is coupled to pen-shaped handle 31 with a fastener 23.

Figure 7:
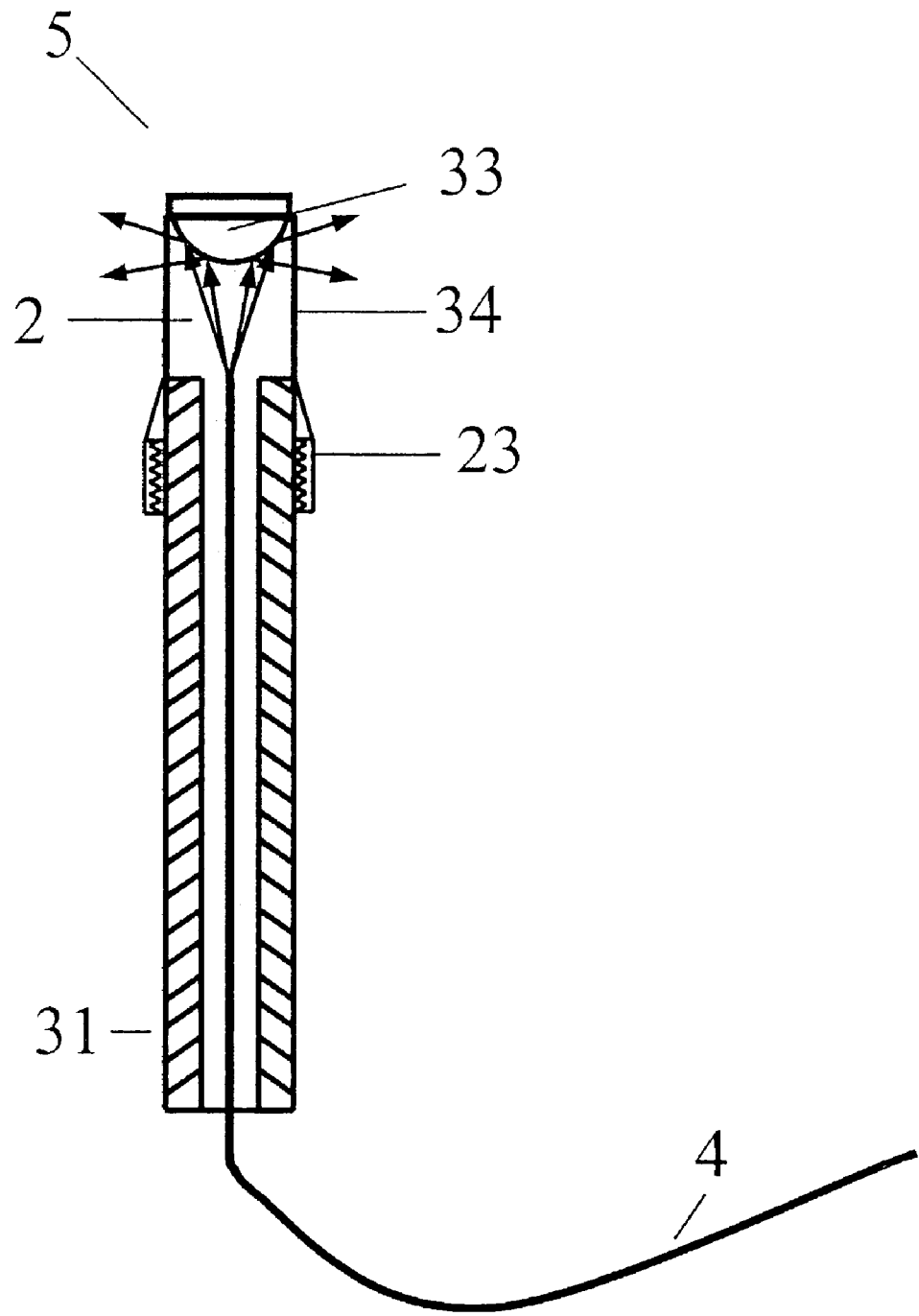
FIG. 7 illustrates an exemplary implementation of the patient interface according to an embodiment of the invention.

FIG. 7 illustrates another embodiment of patient interface 5, which is suitable for the circular treatment of a body cavity, for example, the nasal cavity. In this embodiment optical guidance system 4 guides ultraviolet light beam 2 into pen-shaped grip 31, where it is reflected by circular reflector 33 in a circular manner. Circular reflector 33 can be, for example, a conical or a spherical reflecting surface. Circular applicator head 34, housing circular reflector 33, is coupled to pen-shaped handle 31 with fastener 23. Body cavities, such as the nasal cavity can be treated with this embodiment in a circular manner.

Figure 8:
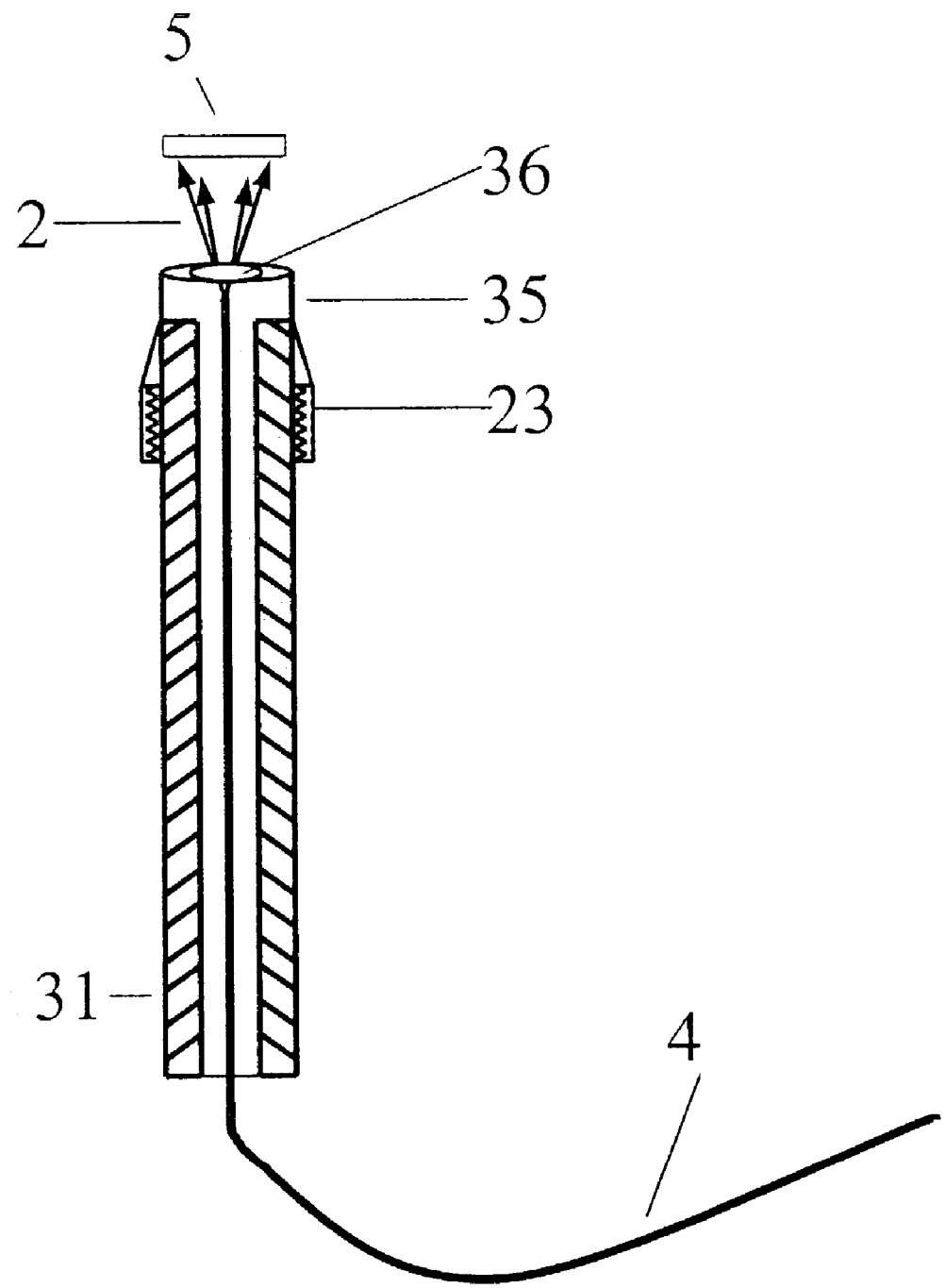
FIG. 8 illustrates an exemplary implementation of the patient interface according to an embodiment of the invention.

FIG. 8 illustrates another embodiment of patient interface 5, which is suited for a spot treatment of tissue surfaces, such as the nasal mucous membrane. Optical guidance system 4 guides ultraviolet light beam 2 into pen-shaped handle 31, where it is guided onto a spot on the tissue to be treated by spot applicator 36. Spot applicator 36 can be, for example, a plano-parallel disk or a lens 36 made of quartz or plastic transparent to ultraviolet light. Spot applicator 36 is housed by spot applicator head 35, which is fastened onto pen-shaped handle 31 by a fastener 23.

Figure 9:
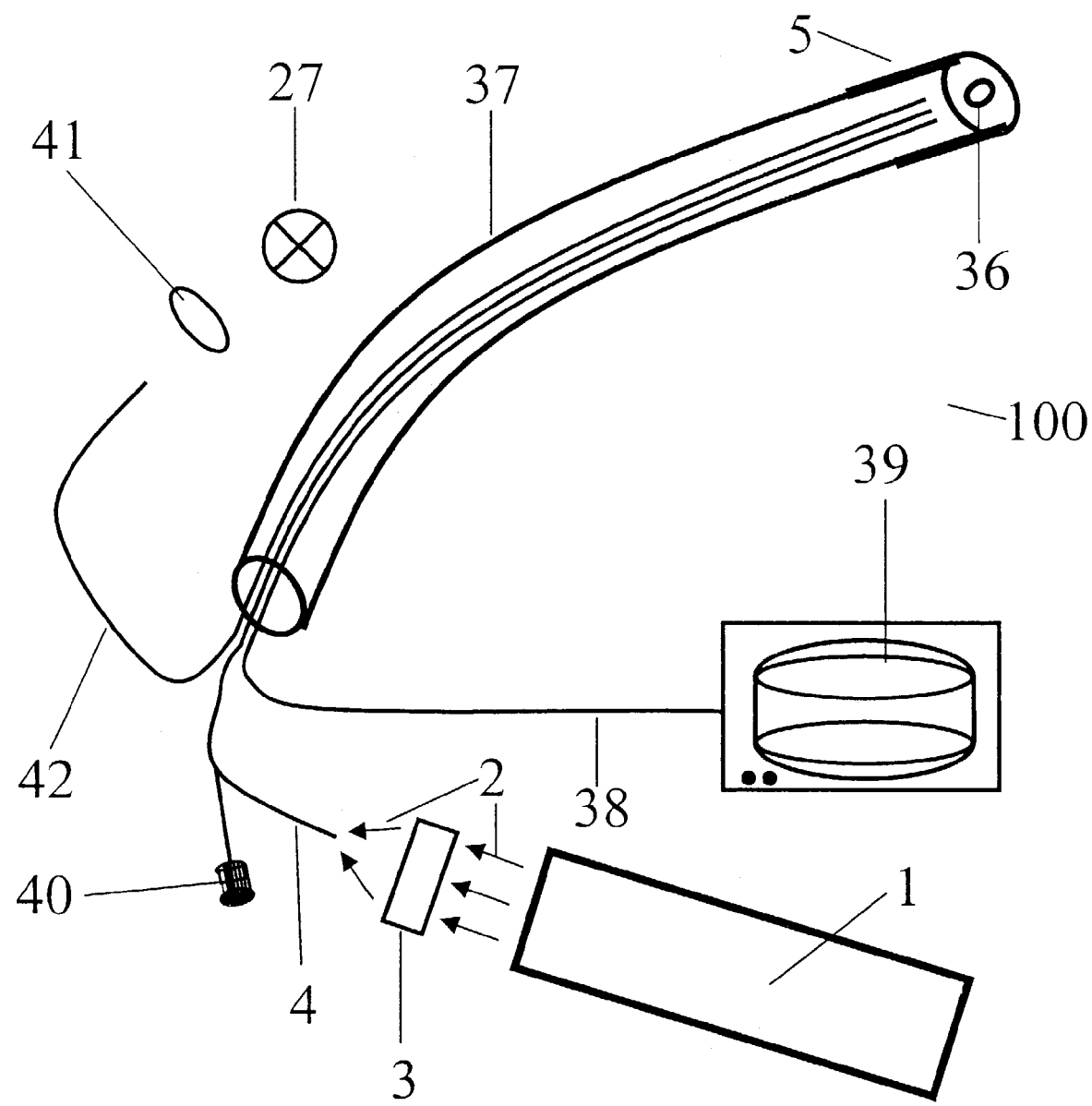
FIG. 9 illustrates a phototherapeutical apparatus including a flexible endoscope, according to an embodiment of the invention.

FIG. 9 illustrates another embodiment of patient interface 5, which is suited for a spot treatment of tissue surfaces, such as the nasal mucous membrane. Ultraviolet light beam 2 generated by ultraviolet light source 1 is focused and coupled by optical coupling unit 3 into optical guidance system 4. Optical guidance system is integrated into flexible endoscope 37. Flexible endoscope 37 is capped with patient interface 5. Patient interface 5 includes a spot applicator 36. Spot applicator 36 can be, for example, a plano-parallel disk or a lens 36 made of quartz or plastic transparent to ultraviolet light. In some embodiments spot applicator 36 can have a sloped distal end.

In order to illuminate the tissue surface to be treated, an illuminating light is provided by illuminating light source 27. The generated illuminating light is guided through lens 41 into illuminating optical cable 42. Illuminating optical cable 42 can be also integrated into flexible endoscope 37. The illuminating light illuminates the tissue surface to be treated through patient interface 5.

Light reflected from the illuminated tissue surface is conducted back from the illuminated tissue surface via image processing optical cable 38, which can be integrated into flexible endoscope 37 as well. Image processing optical cable 38 is coupled into image processing unit 39 to facilitate visual control of the application of the phototerapeutical apparatus.

In some embodiments optical guidance system 4 can be rotated within flexible endoscope 37 by positioning unit 40, so that the direction of ultraviolet light beam 2 emitted through patient interface 5 can be modified. In other embodiments flexible endoscope 37 itself can be rotated by positioning unit 40. These embodiments are useful for the treatment of various body cavities, for example, a larynx, a digestive canal, and urogenital organs.

Some embodiments for the circular and the spot treatment of tissue surfaces may include a Panoramic Annular Lens (PAL) optical system. A PAL system, transparent to the ultraviolet light can be included into circular applicator head 34 and spot applicator head 35. Including a PAL optical system can be helpful for simultaneous treatment of tissue surfaces and optical image processing.

Phototherapeutical Method

According to embodiments of the invention, a phototherapeutical method 200 is described for the treatment and prevention of inflammatory and hyperproliferative diseases of body cavities, more particularly for the treatment and prevention of common inflammatory diseases of the nasal mucous membrane and paranasal sinuses, including allergic rhinitis (hay fever), vasomotor rhinitis, nonallergic eosinophilic rhinitis, chronic sinusitis (inflammation in the paranasal sinuses), and for the treatment and prevention of hyperproliferative diseases, including nasal polyps (a frequent benign hyperproliferative lesion in chronic inflammatory conditions of the nasal mucous membrane).

Phototherapeutical method 200 is based on the inventor's research results, which showed that the application of ultraviolet light on tissue surfaces in body cavities decreases the number and the activity of inflammatory cells (mast cells, eosinophils, and lymphocytes) responsible for the mediator release and synthesis in the mucous membrane, and thereby it reduces the clinical symptoms of inflammatory, hyperproliferative, and allergic diseases. This effect of the ultraviolet light may be partly due to apoptosis induction.

Embodiments of phototherapeutical method 200 can be practiced on various body cavities. These body cavities include: nasal cavity, paranasal sinus, mouth cavity, throat, esophagus, stomach, small intestine, large intestine, gastrointestinal tract, rectum, ear, trachea, urogenital tract, portio, uterus, and conjunctiva. It is understood that all these embodiments belong to the scope of the application.

Figure 10:
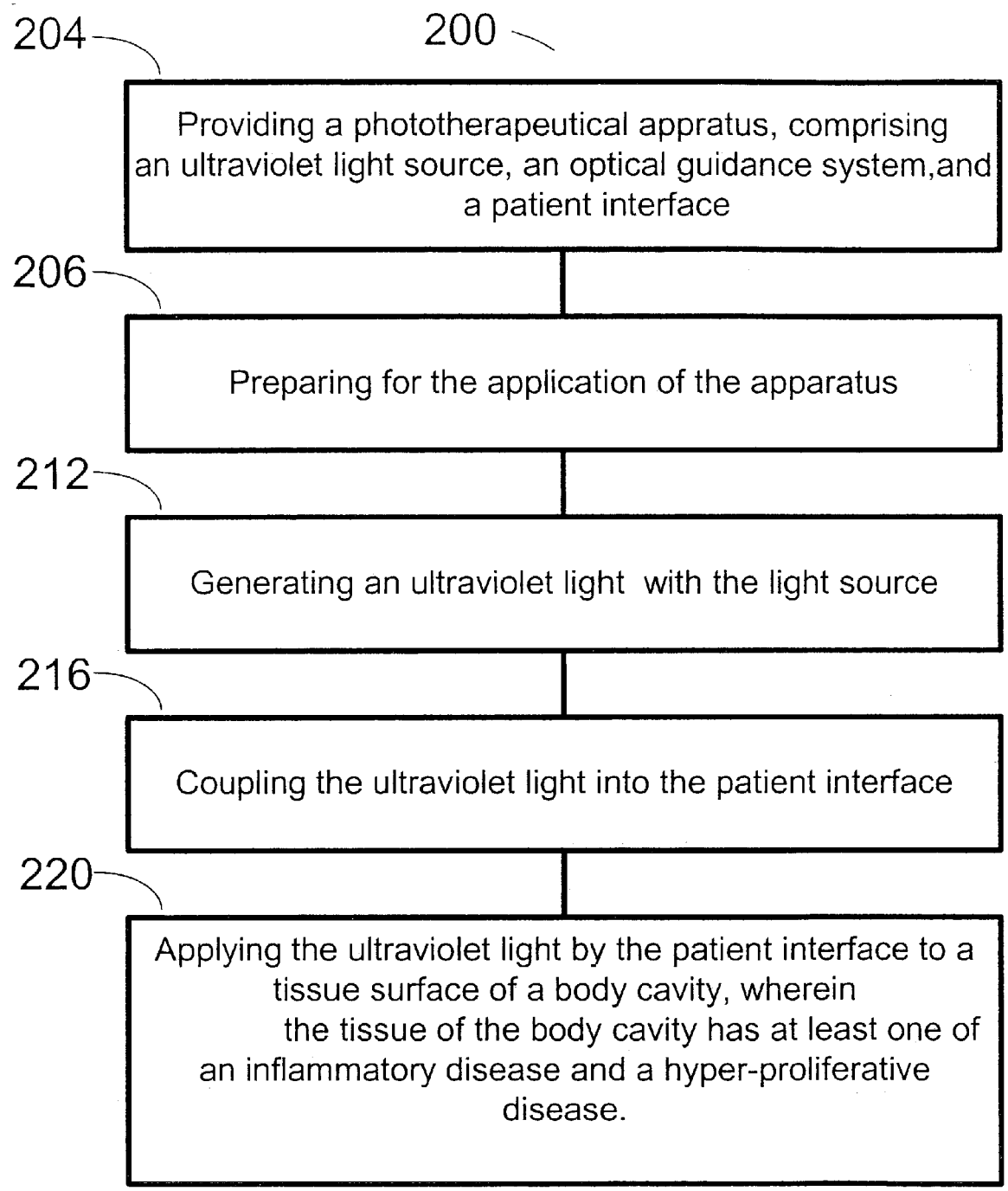
FIG. 10 illustrates steps of the phototherapeutical method, according to an embodiment of the invention.

FIG. 10 illustrates steps of phototherapeutical method 200. In step 204 phototherapeutical apparatus 100 is provided, wherein phototherapeutical apparatus 100 includes: ultraviolet light source 1, optical guidance system 4, coupled to ultraviolet light source 1, and patient interface 5, coupled to optical guidance system 4. Phototherapeutical method 200 can be practiced with any embodiment of phototherapeutical apparatus 100, described earlier.

In step 204 some embodiments of photoherapeutical apparatus 100 include essentially monochromatic ultraviolet light sources, other embodiments include multiwavelength ultraviolet light sources. In some embodiments of photoherapeutical apparatus 100 the monochromatic light source was a xenon chloride excimer laser with a wavelength of 308 nm. It was found that a 308 nm xenon chloride laser induces dose and time-dependent T-cell apoptosis. Further, it was found that applying a xenon chloride laser induces the apoptosis of T-cells at a significantly higher rate than applying a narrow-band UVB (NB-UVB) light.

Other embodiments of phototherapeutical apparatus 100 utilize other monochromatic ultraviolet light sources, for example, a nitrogen laser, a frequency multiplied Nd-YAG laser, a xenon fluoride excimer laser, any type of ultraviolet diode lasers, or any other laser, which emits light in the ultraviolet spectrum.

Yet other embodiments include multiple wavelengths ultraviolet light sources, for example, discharge lamps and arc lamps. Each of these lamps can be filled, for example, with xenon, mercury vapour, and a mixture of xenon and mercury vapour. Other embodiments include fluorescent lamps, NB-UVB lamps, ultraviolet light emitting diodes (UV-LEDs), and dye lasers.

In step 206 a preparation for the treatment by phototherapuptical method 200 is performed. The preparation can include determining a light threshold of the particular patient on a part of the patient's skin, which was not recently exposed to sunlight. One measure of a light threshold is the Minimal Erythema Dose (MED). The MED is the smallest dose of ultraviolet light, which causes erythema on the patient's previously unexposed skin after 24 hours. The MED is then used to determine the value of the first dose, applied to the area to be treated.

The preparation can further include selecting a suitable patient interface 5 for practicing phototherapeutical method 200. This choice depends, for example, on the location of the area of the tissue surface to be treated and the anatomy of the body cavity of the patient.

In step 212 ultraviolet light is generated by ultraviolet light source 1.

In step 216 the generated ultraviolet light is coupled into patient interface 5 through optical guidance system 4.

In step 220 the generated ultraviolet light is applied by patient interface 5 to a tissue surface of a body cavity. In some embodiments of the method, the previously determined MED value is used to determine the first dose, applied to the tissue surface to be treated.

In some embodiments of the method, step 220 includes inserting patient interface 5 at least partially into the body cavity. Patient interface 5 is inserted at the distal end.

In some embodiments of step 220, where the tissue surface is the nasal mucous membrane, an ultraviolet light was applied through patient interface 5 with a dose between about 20 mJ/cm$^2$ and about 1000 mJ/cm$^2$, depending on the type of the ultraviolet light source itself. The treatment with ultraviolet light can be repeated one or more times per week. The repeated application of ultraviolet light can be performed with the same dose or with increasing doses, depending on the patient's tolerance and on the improvements of the clinical symptoms.

Research indicated that the clinical symptoms of the treated nasal mucous membrane improved considerably with the treatment. These symptoms include nasal blockage, nasal itch, nose running, sneezing, and itching of the palate in patients with allergic rhinitis.

Figure 11:
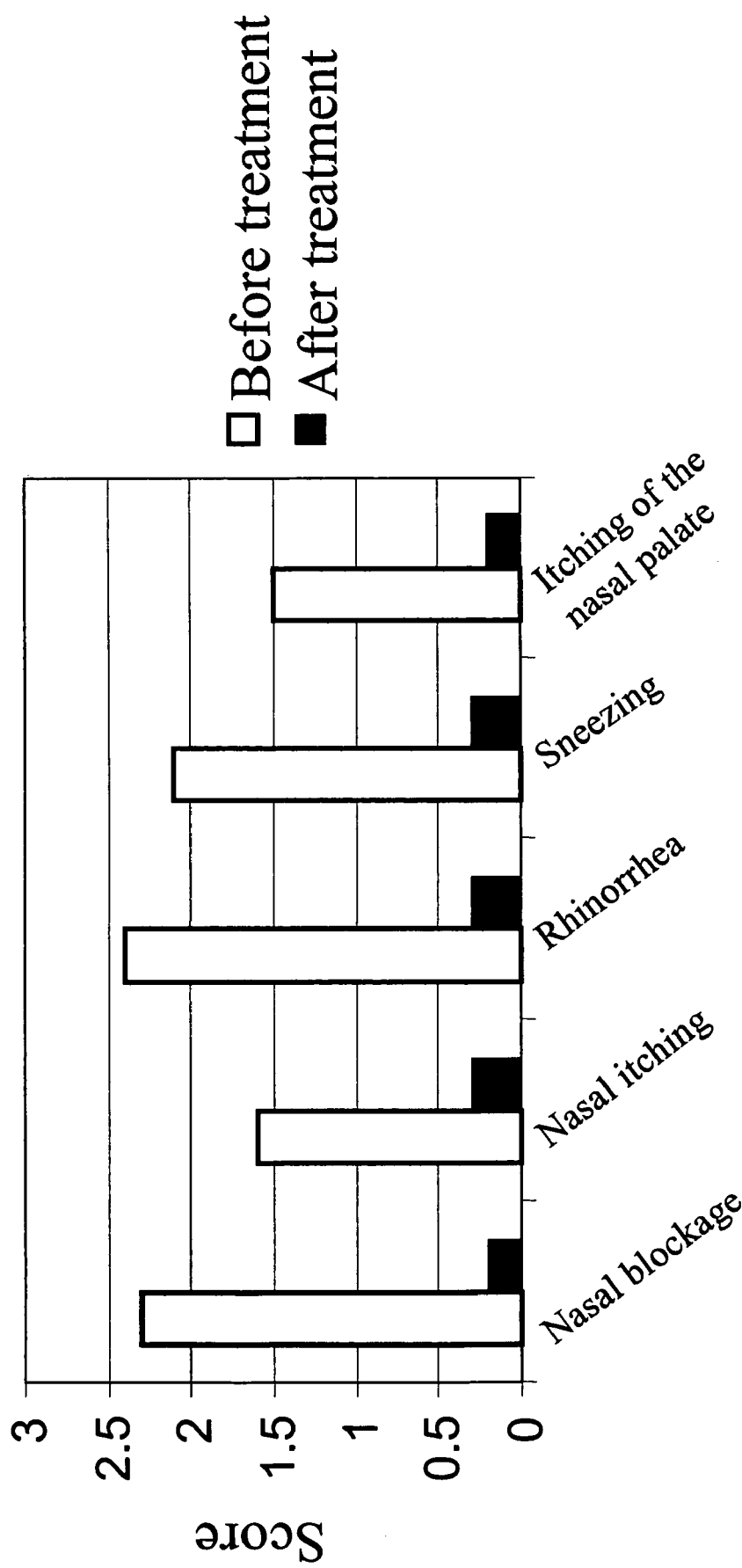
FIG. 11 illustrates the decrease of clinical symptoms due to treatment with an embodiment of the phototherapeutical method.

FIG. 11 illustrates the improvement of hay fever symptoms of the nasal mucous membrane as a result of being treated by phototherapeutic method 200. The illustrated embodiment of method 200 used a 308 nm xenon chloride laser. The severity scores of hay fever (0=no symptoms, 3=very severe symptoms) are shown before the treatment and after a 3-week treatment. The treatment included using the same dose twice per week. As shown, the clinical symptoms and complaints of the patients decreased significantly after the treatment.

Similar improvements were observed in the clinical symptoms of vasomotor rhinitis, nonallergic eosinophilic rhinitis, chronic sinusitis, and in the sizes of nasal polyps after treatment with phototherapeutical method 200. The clinical symptoms decreased considerably after the treatment.

In some embodiments the preparation of step 206 includes increasing the efficacy of phototherapeutical method 200 by administering photosensitizing substances before the phototherapy. Sometimes this method is referred to as photochemotherapy. An example for photosensitizing substances is psoralens, including 5-methoxypsoralen, 8-methoxypsoralen, and trimethoxypsoralen. These materials can be used in concentrations between about 0.0005% and about 0.5%, furthermore they can be applied in creams or in solutions.

When a photosensitizing substance is applied in step 206, the minimal phototoxicitiy dosis (MPD) can be measured on a part of the patient's skin, which was not exposed to sunlight before starting the therapy. The MPD is the smallest ultraviolet dose, which induces erythema on a previously unexposed photosensitized skin after 72 hours.

In step 220 ultraviolet light is applied to the nasal mucous membrane, which was photosensitized with the same photosensitizing substance as in step 206. The application can be started with a dose about 0.1×MPD to about 5.0×MPD, depending on the severity of the symptoms of the patient. During repeated applications in some embodiments the dose remains approximately constant. In other embodiments the dose is increased depending on the patient's tolerance. Step 220 can be repeated once or several times per week.

Research showed that practicing photochemotherapy through steps 206–220 by applying photosensitizing materials inhibits rapidly and effectively the clinical symptoms of hay fever, including nasal blockage, nasal itch, nose running, sneezing and itching of the palate.

Figure 12:
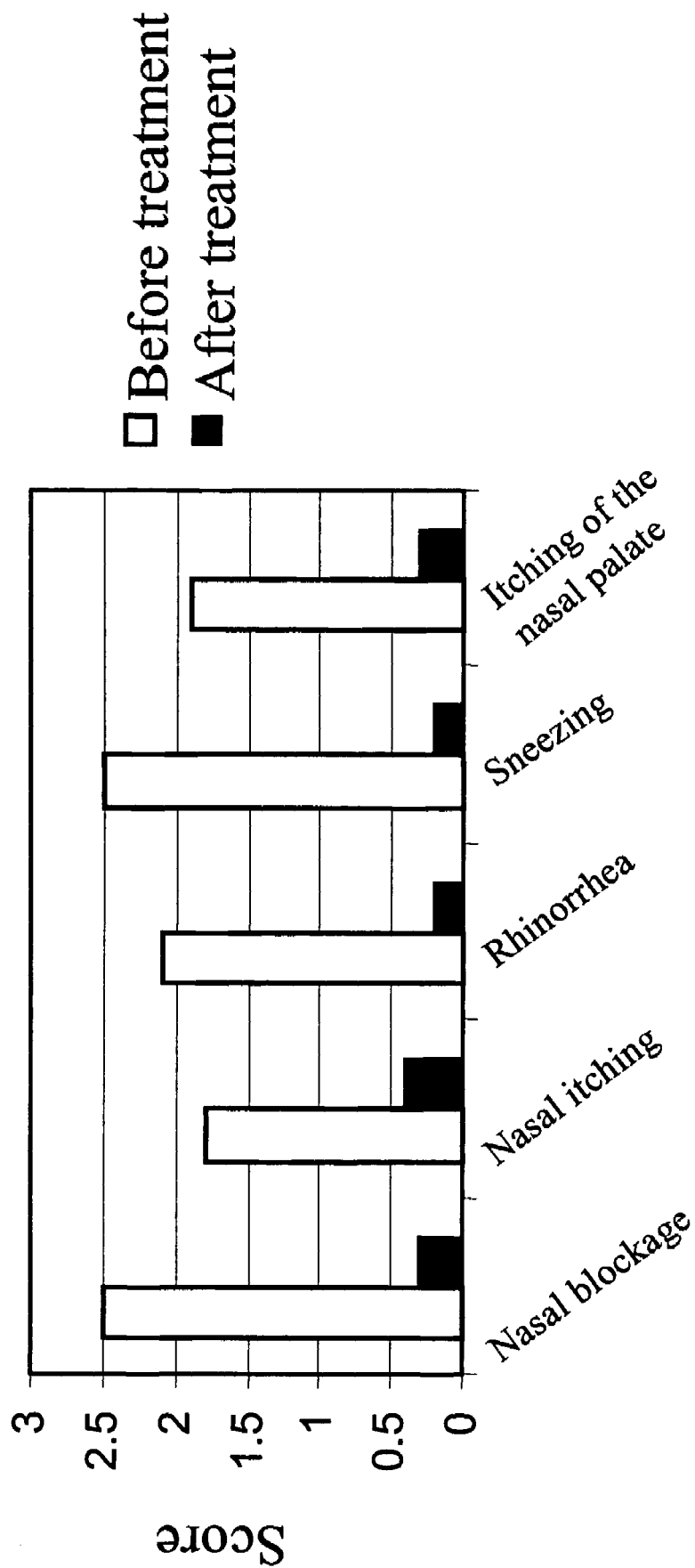
FIG. 12 illustrates the decrease of clinical symptoms due to treatment with an embodiment of the photochemotherapeutical method.

FIG. 12 illustrates the improvement of hay fever symptoms of the nasal mucous membrane as a result of being treated by photochemotherapeutic method 200. This embodiment of the method used a 308 nm xenon chloride laser. The severity scores of hay fever (0=no symptoms, 3=very severe symptoms) are shown before the treatment and after a 3-week treatment. The treatment was applied twice per week with essentially constant doses. All the clinical symptoms and complaints of the patients decreased substantially after the photochemotherapy.

Similar improvements are observed in the clinical symptoms of vasomotor rhinitis, nonallergic eosinophilic rhinitis, chronic sinusitis, and the sizes of nasal polyps considerably decreased after ultraviolet photochemotherapy.

Phototherapeutical method 200 is also suitable for the prevention of inflammatory and hyperproliferative diseases of body cavities. For example, in the case of seasonal allergic rhinitis phototherapeutical method 200 can be started before the appearance of the clinical symptoms. In this embodiment, the prevention is also based on the minimal erythema dose (MED) of the patient and can be administered once or several times per week.

Similarly, phototherapeutical method 200 with photochemotherapy is also suitable for the prevention of the clinical symptoms of patients with seasonal allergic rhinitis. The treatment can be started before the appearance of the symptoms. For prevention, phototherapeutical method 200 can be started with doses between 0.1×MPD and 2×MPD, depending on the severity of the allergy. The treatment can be administered once or several times per week depending on the tolerance of the patient.

Finally it is noted that the application of phototherapeutical method 200 is significantly cheaper than presently practiced drug based treatments.

Potential Side Effects

Ultraviolet light might facilitate the appearance of viral and bacterial infections on the treated areas because of its immunosuppressive effect. This effect is similar to the effect of topical corticosteroides. However, the likelihood for these infections is lower than that of the presently used local immuno-suppressive preparations, because ultraviolet light also has a direct microbicidal effect (Folwaczny M, Liesenhoff T, Lehn N, Horch H H: Bactericidal action of 308 nm excimer-laser radiation: an in vitro investigation. J Endodontics, 24: 781–785, 1998). Furthermore, ultraviolet light also increases the direct microbicidal activity of epithelial cells (Csató M, Kenderessy SzA, Dobozy A: Enhancement of Candida albicans killing activity of separated human epidermal cells by ultraviolet radiation. Br J Dermatol 116: 469–475, 1987).

Further, it is well known that repeated irradiation by ultraviolet light in high doses has carcinogenic potency. However, the carcinogenic effect of ultraviolet light is connected with the cumulative dose. of the ultraviolet light over years. Since the irradiation doses administered during phototherapeutical method 200 are much lower than the known carcenogenically significant doses, the risk of carcinogenesis is barely increased by the present phototherapeutical method 200.

Practicing phototherapeutical method 200 with phototherapeutical apparatus 100 is further illustrated through the following examples.

EXAMPLE 1

The symptoms of a patient suffering from ragweed-induced hay fever 10 years ago did not respond to the used antihistamine and topical corticosteroid nasal drops satisfactorily. At examination the patient complained of severe nasal blockage, nasal itching, nose running, frequent sneezing and itching of the nasal palate. On an area of the back of the patient, which was not recently exposed to sunlight, the minimal erythema dosis (MED) was determined to be about 200 mJ/cm$^2$, using a 308 nm xenon chloride laser as ultraviolet light source. One day later the phototherapy of the nasal mucous membrane was started. For this purpose ultraviolet light beam 2 of ultraviolet light source 1 was directed by optical focusing into optical guidance system 4. Optical guidance system 4 was an optical cable made of quartz and it had a diameter of 1.6 mm. The optical cable was connected to patient interface 5 of the type shown in FIG. 4. Output window 26 of patient interface 5 included a plano-parallel transparent plastic disk with a diameter of 4 mm. The nasal mucous membrane of the patient was irradiated with a dose of 100 mJ/cm$^2$ through output window 26. The irradiation was performed with a frequency of 1 Hz, wherein the length of the impulses were 15 ns and the energy of one impulse at output window 26 of patient interface 5 was 1.79 mJ. Reckoning with the diameter of output window 26 of 4 mm, its surface was 0.1256 cm$^2$, so the energy density of the irradiation was 14.25 mJ/cm$^2$. Altogether seven impulses were administered to provide a total dose of about 100 mJ/cm$^2$. In each nostril 16 areas were irradiated.

The treatment was controlled visually under protection of ultraviolet protecting glasses using the visible light beam of illuminating light source 27 mounted into handgrip 20 of patient interface 5. The complete time of a treatment was 5 minutes, including the time necessary to change the position of patient interface 5. The treatment did not cause any complaint by the patient. This treatment was repeated two times per week using the same phototherapeutical apparatus, but the irradiation dose was increased by 50 mJ/cm$^2$ weekly. After the second treatment the symptoms and complaints of the patient decreased to a large extent and in the third week after the sixth treatment the patient was completely free of symptoms. The treatment was stopped and no recurrence was observed. The treatment was quick and caused no complaint from the patient. The patient did not receive any drugs during the treatment. In comparison to the therapies used earlier, phototherapy was found to be more efficacious by the patient.

EXAMPLE 2

Phototherapeutical treatment was also performed on patients with perennial allergic rhinitis, which was induced by house dust mite and whose treatment with antihistamine and local steroids proved to be ineffective. The phototherapy was performed with xenon chloride excimer laser of wavelength of 308 nm.

The MED was measured for each patient and phototherapy was started with 0.5×MED doses. Circular applicator head 34 for cylindrically symmetric treatment was inserted into the meatus nasi inferior area of the nasal cavity for the treatment, then a cylindrically symmetric irradiation was administered onto the tissue surface with the xenon chloride laser. The length of impulses was 15 ns, the frequency of irradiation was 10 Hz. The energy density of each impulse was 2 mJ/cm$^2$. The administering of the dose of 100 mJ/cm$^2$ took 5 seconds. Circular applicator 34 was then inserted into middle and thereafter into the upper part of the nasal cavity and the treatment was repeated in these positions in the same way. The treatment of the right and left nasal cavities took up approximately 2 minutes. The treatment was repeated with the same doses two times per week. After the eighth treatment the clinical symptoms of the hay fever improved considerably at each patient, whereas no side effects were observed.

EXAMPLE 3

The severe symptoms of a patient suffering from ragweed-induced hay fever did not improved satisfactorily after using antihistamines and topical corticosteroid nasal drops. At examination the symptoms (nasal blockage, nasal itching, nose running, frequent sneezing, and itching of the nasal palate) of the patient were severe, therefore phototherapeutical method 200 was performed with photochemotherapy. The minimal phototoxicity dose was measured on the forearm of the patient not exposed to sunlight. Ultraviolet light source 1 of the type shown in FIG. 2 was used for the irradiation in a way that two ultraviolet light beams of wavelengths between 310 and 350 nm were coupled into optical guidance system 4 through optical filters. The MPD was 500 mJ/cm$^2$ and the treatment of the nasal mucous membrane was started with a dose of 2.0×MPD (=1000 mJ/cm$^2$) using patient interface 5 shown in FIG. 4. Photochemotherapy was performed after using 8-methoxypsoralen nasal spray. Head 25 of patient interface 5 shown in FIG. 4 was inserted into the nasal cavity and the nasal mucous membrane was irradiated with the dose of 1000 mJ/cm$^2$. The power density of ultraviolet light beam 2 was 43.2 mW/cm$^2$ through output window 26 of patient interface 5. The treatment was visually controlled under protection of ultraviolet protecting eyeglasses using the visible light beam of illuminating light source 27.

Patient interface 5 was brought into contact with the nasal mucous membrane altogether in eight positions in each nostril. The treatment of the nostrils took approximately 3 minutes and caused no complaints from the patient. This photochemotherapy was repeated once per week. The symptoms of the patient improved considerably after the second treatment already and after the third treatment the patient was completely free of symptoms. The treatment was stopped after the fourth treatment. After the therapy the symptoms of the patient did not return.

EXAMPLE 4

A patient had a large polyp in the left nostril, which did not improve after administering local corticosteroids. The polyp caused chronic sinusitis, therefore phototherapeutical method 200 was performed with a xenon chloride laser. The minimal erythema dose (MED) was determined on the back of the patient, which proved to be 250 mJ/cm$^2$. For the purpose of phototherapy ultraviolet light beam 2 of wavelength of 308 nm was coupled into optical guidance system 4 after focusing. Optical guidance system 4 was a quartz ultraviolet light conducting cable of diameter 0.5 mm. Optical guidance system coupled ultraviolet light beam 2 into patient interface 5 of the type shown in FIG. 8. Plano-parallel disk 36 of thickness of 2 mm made of transparent plastic of patient interface 5 was brought into contact with the surface of the polyp and a round area of diameter 2 mm was irradiated with the dose of 750 mJ/cm$^2$. The irradiation was conduced at the frequency of 5 Hz, the length of impulses was 15 ns, the energy of impulse was 1.96 mJ. Altogether twelve impulses were issued to administer an irradiation dose of 750 mJ/cm$^2$. Five days after one single treatment the nasal polyp disappeared without any scar formation. All complaints of the patient disappeared as well.

EXAMPLE 5

In a patient with chronic rhinosinusitis with unknown origin different drugs, including antihistamines, corticosteroids, and antibiotics were used, but proved to be ineffective. Therefore, phototherapeutical method 200 was administered. Ultraviolet light source 1 of the type shown in FIG. 2 was used for the treatment. The minimal erythema dosage (MED) was first determined on the forearm of the patient not exposed to sunlight earlier, then the phototherapeutical treatment of the nasal mucous membrane was started with a dose of 140 mJ/cm$^2$. Plano-parallel disk 36 of diameter of 4 mm of the patient interface 5 shown in FIG. 4 was brought into contact with the affected mucous membrane and this surface was irradiated during the treatment. The treatment was controlled visually under protection of ultraviolet protecting eyeglasses using the visible light of illuminating light source 27. Ultraviolet light was administered in altogether eight positions per nostril to irradiate the affected mucous membrane. This phototherapy was repeated several times per week. After the sixth treatment the symptoms of the patient decreased considerably, and after the tenth treatment the patient became free of symptoms. One month after stopping the therapy the patient was still free of symptoms.

Although the present invention and its advantages have been described in detail, it should be understood that various changes, substitutions, and alterations can be made therein without departing from the spirit and scope of the invention as defined by the appended claims. That is, the discussion included in this application is intended to serve as a basic description. It should be understood that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Neither the description nor the terminology is intended to limit the scope of the claims.

What is claimed is:

1. A phototherapeutical apparatus, comprising:
   an ultraviolet multiwavelength light source, operable to generate ultraviolet light with a wavelength in the range of about 280 nm to about 400 nm;
   an optical guidance system, operable to receive and guide the ultraviolet light of the light source; and
   a patient interface, operable
      to receive the guided light from the optical guidance system; and
      to be inserted at least partially into a small body cavity, wherein the multiwavelength light source comprises:

a quartz bulb, operable to generate ultraviolet light, the quartz bulb comprising:
electrodes, defining a discharge volume of 0.1 mm$^3$ to 1 mm$^3$, coupled to a power supply; and
gas.

2. The phototherapeutical apparatus of claim 1, wherein the multiwavelength light source comprises:
a concave mirror, reflecting a part of the ultraviolet light generated by the quartz bulb;
a focusing lens, operable to focus a part of the generated ultraviolet light and a part of the reflected ultraviolet light; and
an optical filter, operable to receive and filter the focused light.

3. The phototherapeutical apparatus of claim 1, wherein the quartz bulb further comprises at least one of a fluorescent lamp, an arc lamp, and an electric discharge wherein the electric discharge lamp comprising at least one of xenon, argon, and mercury vapor.
an ultraviolet multiwavelength light source, selected from the group of a fluorescent lamp, an ultraviolet light emitting diode, a dye laser, an arc lamp, and an electric discharge lamp, the electric discharge lamp comprising at least one of xenon, argon, and mercury vapor, operable to generate ultraviolet light with a wavelength in the range of about 280 nm to about 400 nm;
an optical guidance system, operable to receive and guide the ultraviolet light of the light source; and
a patient interface, operable
to receive the guided light from the optical guidance system; and
to be inserted at least partially into a small body cavity, the phototherapeutical apparatus comprising an optical coupling unit, wherein the optical coupling unit comprises:
a targeting light source, operable to provide a targeting light;
a dichroic mirror, operable to receive the ultraviolet light and the targeting light, and to direct the received lights in a preset direction; and
a lens system, operable
to receive the directed lights from the dichroic mirror; and
to couple the received directed lights into the optical guidance system;
wherein the patient interface comprises
a handgrip, wherein the optical guidance system is coupled into the handgrip;
an optical tube, receiving the guided ultraviolet light and the guided targeting light, guided by the optical guidance system;
an illuminating light source, operable to provide an illuminating light through a head; and
a mirror, mounted in the optical tube, operable to direct the guided ultraviolet light and the guided targeting light through the head onto the tissue surface of the body cavity, wherein the patient interface comprises
a magnifying lens, positioned to receive a reflected illuminating light, reflected from the tissue surface of the body cavity.

4. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein
the tissue is a mucous membrane and the body cavity is at least one of
a mouth cavity, a throat, an esophagus, a stomach, a small intestine, a large intestine, a gastrointestinal tract, a rectum, an ear, a trachea, a urogenital tract, a portio, a uterus, and a conjunctiva.

5. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein
the tissue is a mucous membrane and the body cavity is at least one of a nasal cavity and a paranasal sinus.

6. The method of claim 5, wherein the inflammatory disease is at least one of
allergic rhinitis, vasomotor rhinitis, nonallergic eosinophilic rhinitis, rhinosinusitis, and sinusitis.

7. The method of claim 5, wherein the hyper-proliferative disease is a nasal polyp.

8. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm in a time interval of 1–10 minutes, wherein
the tissue of the body cavity has at least one of an inflammatory disease and a hyper-proliferative disease, wherein the preparation for the application of the photoherapeutical apparatus comprises
determining at least one of a minimal erythema dose and a minimal phototoxicity dose.

9. The method of claim 8, wherein the applying the ultraviolet light to the tissue surface of the body cavity comprises
applying the ultraviolet light in a dose calculated in relation to at least one of the minimal erythema dosis and the minimal phototoxicity dose.

10. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein the preparation for the application of the photoherapeutical apparatus comprises
applying a photosensitizer substance to the tissue surface, wherein the photosensitizer substance is at least one of 5-methoxypsoralen, 8-methoxypsoralen, and tri-methoxysporalen.

11. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein the preparation for the application of the photoherapeutical apparatus comprises
applying a photosensitizer substance to the tissue surface, wherein
the applying the photosensitizer substance comprises
applying the photosensitizer substance to the tissue surface in the form of at least one of a spray and a cream.

12. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein the preparation for the application of the photoherapeutical apparatus comprises
applying a photosensitizer substance to the tissue surface, wherein
the applying the photosensitizer substance comprises
applying the photosensitizer substance to the tissue surface in a concentration between approximately 0.0005% and 0.5%.

13. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small body cavity to deliver a dose in the range of 20–1000 mJ/cm$^2$ in a time interval of 1–10 minutes, wherein
the tissue of the body cavity has at least one of an inflammatory disease and a hyper-proliferative disease, wherein
the preparation for the application of the photoherapeutical apparatus comprises
applying a vasoconstrictor substance to the tissue surface.

14. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a small cavity to deliver a dose in the range of 20–1000 mJ/cm$^2$ in a time interval of 1–10 minutes, wherein
the tissue of the body cavity has at least one of an inflammatory disease and a hyper-proliferative disease, wherein
the applying the ultraviolet light to the tissue surface comprises applying the ultraviolet light to the tissue surface repeatedly.

15. The method of claim 14, wherein the applying the ultraviolet light to the tissue surface repeatedly comprises
applying the ultraviolet light repeatedly with at least one of the same dose and an increasing dose, wherein
the increasing dose increases with 10% to 20% percent per application, depending on the tolerance of the patient.

16. The method of claim 14, wherein the applying the ultraviolet light to the tissue surface repeatedly comprises
applying the ultraviolet light to the tissue surface once, twice, or three times a week.

17. The phototherapeutical method of claim 14, wherein an inner diameter of the small body cavity is less than 1 centimeter.

18. A method of treating diseases, the method comprising:
providing a phototherapeutical apparatus, comprising:
an ultraviolet light source;
an optical guidance system, coupled to the ultraviolet light source; and
a patient interface, coupled to the optical guidance system; preparing for the application of the phototherapeutical apparatus; inserting the patient interface at least partially into a nasal cavity;
generating ultraviolet light with the ultraviolet light source;
coupling the generated ultraviolet light into the patient interface through the optical guidance system; and
applying the ultraviolet light by the patient interface to a tissue surface of the nasal cavity, wherein
the tissue of the nasal cavity has allergic rhinitis.

19. A method of preventing diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system;
applying the ultraviolet light by the patient interface to a tissue surface of a body cavity, wherein
the tissue of the body cavity is symptom-free.

20. The method of claim 19, wherein the applying the ultraviolet light by the patient interface comprises
inserting the patient interface at least partially into the body cavity.

21. The method of claim 19, wherein the preventing diseases comprises
preventing at least one of an inflammatory disease and a hyper-proliferative disease.

22. The method of claim 19, wherein the preventing diseases comprises
preventing a disease of at least one of a mucous membrane of a nasal cavity and a nasal sinus.

23. The method of claim 19, wherein the preventing diseases comprises preventing rhinitis allergica.

24. A method of treating diseases, the method comprising:
providing a photoheapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a body cavity, wherein
the tissue of the body cavity has at least one of an inflammatory disease and a hyper-proliferative disease; and
the multiwavelength light source is one of a fluorescent lamp, a ultraviolet light emitting diode, a dye laser, an arc lamp, and an electric discharge lamp, the electric discharge lamp comprising at least one of xenon, argon, and mercury vapor, generating a quasi continuous light with a frequency less than about 10 Hertz.

25. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and
applying the ultraviolet light by the patient interface to a tissue surface of a body cavity, wherein
the tissue of the body cavity has at least one of an inflammatory disease and a hyper-proliferative disease; and
the tissue is a mucous membrane and the body cavity is at least one of a mouth cavity, a throat, an esophagus, a stomach, a small intestine, a large intestine, a gastrointestinal tract, a rectum, an ear, a trachea, a urogenital tract, a portio, a uterus, a conjunctiva, a nasal cavity and a paranasal sinus.

26. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
generating ultraviolet light with the ultraviolet light source;
coupling the generated ultraviolet light into the patient interface through the optical guidance system; and applying the ultraviolet light by the patient interface to a tissue surface of a body cavity, wherein
the tissue of the body cavity has at least one of an allergic rhinitis, vasomotor rhinitis, nonallergic eosinophilic rhinitis, rhinosinusitis, sinusitis, and nasal polyp.

27. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus;
determining at least one of a minimal erythema dosis and a minimal phototoxicity dosis;
generating ultraviolet light with the ultraviolet light source;
coupling the generated ultraviolet light into the patient interface through the optical guidance system; and
applying the ultraviolet light in a dose calculated in relation to at least one of the minimal erythema dosis and the minimal phototoxicity dose by the patient interface to a tissue surface of a body cavity, wherein
the tissue of the body cavity has at least one of an inflammatory disease and a hyper-proliferative disease.

28. A method of treating diseases, the method comprising:
providing a phototherapeutical apparatus, comprising:
an ultraviolet light source;
an optical guidance system, coupled to the ultraviolet light source; and
a patient interface, coupled to the optical guidance system;
preparing for the application of the phototherapeutical apparatus, comprising at least one of:
applying one of 5-methoxypsoralen, 8-methoxypsoralen, and trimethoxysporalen to the tissue surface;
applying a photosensitizer substance to the tissue surface in the form of at least one of a spray and a cream;
applying a photosensitizer substance to the tissue surface in a concentration between approximately 0.0005% and 0.5%; and
applying a vasoconstrictor substance to the tissue surface;
generating ultraviolet light with the ultraviolet light source;
coupling the generated ultraviolet light into the patient interface through the optical guidance system; and
applying the ultraviolet light by the patient interface to a tissue surface of a body cavity, wherein
the tissue of the body cavity has at least one of an inflammatory disease and a hyper-proliferative disease.

* * * * *

UNITED STATES PATENT AND TRADEMARK OFFICE
CERTIFICATE OF CORRECTION

PATENT NO. : 7,226,470 B2  Page 1 of 1
APPLICATION NO. : 10/410690
DATED : June 5, 2007
INVENTOR(S) : Lajos Kemény et al.

It is certified that error appears in the above-identified patent and that said Letters Patent is hereby corrected as shown below:

In Claim 3, at Column 15, lines 15-18, please delete:

"of claim 1, wherein the quartz bulb further comprises at least one of a fluorescent lamp, an arc lamp, and an electric discharge wherein the electric discharge lamp".

In Claim 3, at Column 15, lines 18-19, please delete: "at least one of xenon, argon, and mercury vapor.".

In Claim 9, at Column 17, line 9, please change: "dosis" to --dose--.

In Column 19, claim 17, please delete: "Claim 17".

In Claim 27, at Column 21, line 16, please change: "dosis" to --dose--.

In Claim 27, at Column 21, line 17, please change: "dosis" to --dose--.

In Claim 27, at Column 21, line 24, please change: "dosis" to --dose--.

In Column 22, line 29, please add:

--Claim 29. The phototherapeutical apparatus of claim 1, wherein the quartz bulb further comprises at least one of a fluorescent lamp, an arc lamp, and an electric discharge lamp, wherein the electric discharge lamp comprising at least one of xenon, argon and mercury vapor.--.

Signed and Sealed this

Second Day of September, 2008

JON W. DUDAS
*Director of the United States Patent and Trademark Office*